United States Patent [19]

Dougherty

[11] 4,263,218

[45] Apr. 21, 1981

[54] ALCOHOL-RHODIUM SEPARATION PROCESS

[75] Inventor: Steve J. Dougherty, Sumner, Wash.

[73] Assignee: Union Carbide Corporation, New York, N.Y.

[21] Appl. No.: 81,919

[22] Filed: Oct. 4, 1979

Related U.S. Application Data

[63] Continuation-in-part of Ser. No. 862,555, Dec. 20, 1977, abandoned.

[51] Int. Cl.$^3$ .................... C07C 27/06; C07C 27/34; C07C 27/26
[52] U.S. Cl. ................................ 260/450; 260/449 L
[58] Field of Search ..................... 260/450, 449 L

[56] References Cited

U.S. PATENT DOCUMENTS 4,001,289  1/1977  Dougherty et al. ................ 260/450

Primary Examiner—Howard T. Mars
Attorney, Agent, or Firm—Gary L. Wamer

[57] ABSTRACT

There is described an improvement in the process of recovering alcohol products formed by the homogeneous liquid phase reaction between oxides of carbon and hydrogen in the presence of a rhodium carbonyl complex catalyst which process involves mixing water and an essentially water-immiscible solvent with the solution containing products of such reaction to cause the alcohol products to enter the water phase and the rhodium to enter into the water-immiscible solvent phase wherein the improvement comprises mixing the water, solvent and solution containing products in contact with CO gas.

3 Claims, No Drawings

ALCOHOL-RHODIUM SEPARATION PROCESS

This application is a continuation-in-part of my prior and copending application Ser. No. 862,555, filed Dec. 20, 1977 now abandoned.

This invention is concerned with the recovery of alcohol products from a homogeneous liquid phase mixture containing a rhodium complex. More particularly, this invention relates to the separation of the alcohol products of the reaction between oxides of carbon and hydrogen in a homogenous liquid phase reaction containing a rhodium carbonyl complex.

There are described in U.S. Pat. Nos. 3,833,634 and 3,957,857, for example, processes involving the high pressure reaction of oxides of carbon and hydrogen in the presence of a rhodium carbonyl complex catalyst to produce, as most preferred products, polyhydric alcohols such as ethylene glycol and 1,2-propylene glycol. It has been pointed out in U.S. Pat. No. 3,957,857 that a preferred rhodium carbonyl complex catalyst is a rhodium carbonyl cluster. The nature of that catalyst under the conditions of the reaction or as it is provided to the reaction can be characterized by its infrared spectrum. However, such catalysts frequently take another structure at temperatures and pressures lower than those used in the reaction.

In a preferred embodiment of those processes, the reaction is conducted in a homogenous liquid phase mixture, so that the catalyst and even the alcohol products formed from the reaction are in solution. The solution typically requires the presence of a production solvent mainly to keep the catalyst in solution before and after the reaction. The main, and most valuable, products of those processes are high boiling alkane polyols such as ethylene glycol and the secondary, and less valuable, although nonetheless valuable, products are lower boiling alkanols such as methanol, etc. These products were generally removed by distillation, but in a continuous process rather severe changes would be required from the conditions employed in the high pressure reaction to the conditions employed on separation of product.

However, rhodium carbonyl complexes vary in structure based upon the temperature, solvent, promoter, salt, and carbon monoxide and hydrogen pressure imposed upon them. Therefore, a catalyst complex which may be extremely stable in a solution at one temperature such as during the reaction, could precipitate out of the solution at another temperature such as used during product recovery by distillation.

In the case of large scale processes, significant catalyst losses are unacceptable. In the case of the processes of the U.S. Patents referred to, catalyst losses in the order of, for example, about 0.1% by weight of the rhodium content on a per pass basis would probably make the process uneconomical. This can be better appreciated when one realizes the high current price for rhodium metal. In the commerical practice of these processes it will be necessary to avoid a loss of an amount of rhodium metal which causes the cost of product(s) produced to be greater than the cost of the same product(s) produced by other competitive processes.

U.S. Pat. No. 4,001,289, issued Jan. 4, 1977, describes the separation of alcohol products from a liquid phase homogeneous mixture (the production solution) obtained from the reaction of oxides of carbon and hydrogen in a solvent solution containing a rhodium carbonyl complex catalyst in a manner which minimizes catalyst instability. This is accomplished by mixing the mixture with water and an essentially water immiscible organic extraction solvent for the rhodium complex present in the mixture, forming a water phase containing the alcohol product and an organic solvent phase containing all of the rhodium complex, and separating the phases to effect recovery of product from the water phase without effecting significant catalyst losses since the wate phase is essentially free of the rhodium. U.S. Pat. No. 4,001,289 is incorporated herein by reference.

The present invention is an improvement in the separation process as described in U.S. Pat. No. 4,001,289.

The invention described herein is an improved extraction process for the recovery of the alcohol products produced by these rhodium complex catalyzed reactions which reduces catalyst instability during the recovery phase of a continuous process. By the terms "instability" and "unstable", when referring to the catalyst, it is meant that it is reduced to a condition where it becomes, or is, insoluble in the solution from which the product is being recovered.

The improved process of this invention involves the separation of alcohol products from a liquid phase homogeneous mixture obtained from the reaction of oxides of carbon and hydrogen in a solvent solution containing a rhodium carbonyl complex catalyst. This is accomplished by mixing the liquid phase homogeneous mixture with water and an essentially water immiscible organic extraction solvent for the rhodium complex present in the mixture, forming a water phase containing the alcohol product and an organic solvent phase containing essentially all of the rhodium complex, the improvement comprising mixing the liquid phase homogeneous mixture, water and organic extraction solvent in contact with CO gas.

The term "contact", as used above, means a physical touching of the mixture and carbon monoxide gas as illustrated by providing the gas at the surface of the mixture, or bubbling the gas through the mixture, and the like.

When the liquid phase homogeneous mixture (i.e. the "production solution"), water and the water-immiscible organic extraction solvent are combined in contact with CO gas, a significant reduction in the amount of rhodium lost to the aqueous phase results. Loss of rhodium into the aqueous phase is reduced by as much as 96% (99.97% recovery of rhodium is thus achieved) by carrying out the aforesaid mixing in contact with CO gas.

The typical production solution (i.e., "liquid phase homogeneous mixture") which is to be treated in accordance with this invention will contain the "product(s)" of the reaction, such as the alcohols: ethylene glycol, methanol, ethanol, propanol; esters: ethylene gylcol monoformate, methyl formate, ethyl formate; and the like; the catalyst in the form of a rhodium complex and a production solvent for the catalyst which is also compatible with the products of the reaction. The amount of product in the solution can vary greatly, from about 1 to about 75 weight per cent of the solution. The production solvent can be present in a broad range, such as from about 25 to about 99 weight percent of the solution. The catalyst concentration can vary greatly, from about $1 \times 10^{-6}$ weight percent, or even less, to about 30 weight percent, or more, based on its rhodium metal content. The composition of the liquid homogeneous mixture being treated according to this invention is not narrowly critical. All that is required in the solution (or mixture) is any amount of reaction product which is to be recovered, and any amount of a rhodium complex solvated by a production solvent.

The rhodium complex present in the production solution does not have to have the structure of the rhodium carbonyl complex which catalyzed the reaction between the CO and $H_2$. In those cases where the rhodium carbonyl complex acting as the catalyst has the formula $Rh_{12}(CO)_{30}^{-2}$ and the structure as shown, for example, in U.S. Pat. No. 3,957,857, the rhodium carbonyl complex which exists in the homogeneous mixture may be an anion of the formula $Rh_6(CO)_{16}$ of the structure as shown in said U.S. Pat. No. 3,957,857 or it may be the anion of lower rhodium containing compounds, from monorhodium carbonyl and up. All that is required for the process of this invention is that the rhodium values, as a complex, employed in the reaction, be in solution.

The solubilization of the rhodium carbonyl complex is typically dependent upon the production solvent used to effect the homogeneous mixture. The desired solvent is any liquid material which dissolves or keeps in solution the components of the homogeneous mixture taken from the reactor. It must be solution compatible with the reaction products and the rhodium carbonyl complex.

Illustrative solvents which are generally suitable in making the homogeneous mixture include, for example, ethers such as tetrahydrofuran, tetrahydropyran, diethyl ether, 1,2-dimethoxybenzene, 1,2-diethoxybenzene, the mono-and dialkyl ethers of ethylene gylcol, of propylene glycol, of butylene glycol, of diethylene glycol, of dipropylene glycol, of triethylene glycol, of tetraethylene glycol, of dibutylene glycol, of oxyethylenepropylene glycol, etc; alkanols such as methanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; gammabutyrolactone; deltavalerolactone; substituted and unsubstituted tetrahydrothiophene-1, 1-dioxides (sulfolanes) as disclosed in U.S. application Ser. No. 61,456, filed on July 27, 1979 as a continuation of Ser. No. 615,093, filed Sept. 19, 1975 (now abandoned) which in turn is a continuation-in-part of Ser. No. 537,885, filed Jan. 2, 1975 (now abandoned). The disclosure of said application Ser. No. 61,456 at page 5, beginning with line 24 through page 7, line 21, is incorporated herein by reference.

Also, the crown ethers are suitable herein, particularly those described in U.S. Pat. No. 4,162,261, issued July 24, 1979 (formerly application Ser. No. 832,384, filed Sept. 13, 1977), the disclosure of which in this respect is incorporated herein by reference. The crown ethers described therein contain at least four oxygen heteroatoms and include [18]-crown-6-and [15]-crown-5.

Particularly desirable solvents are tetraglyme, sulfolane, gamma-butyrolactone and the crown ethers. Other very desirable solvents include mixtures of tetraglyme and sulfolane, mixtures of sulfolane and butyrolactone, mixtures of crown ethers and sulfolane, mixtures of crown ethers and tetraglyme, mixtures of crown ethers and butyrolactone, and mixtures of tetraglyme and butyrolactone.

A number of nitrogen containing bases and additionally salts, may be associated with the rhodium carbonyl complex in the homogeneous mixture. They are used to promote the catalyst's activity in the course of reaction. The kinds of each which may be selected is dependent upon the conditions used to effect the reaction between CO and hydrogen. Very high pressure reactions require only soluble rhodium, oxide of carbon (such as carbon monoxide) and hydrogen to form a desirable rhodium carbonyl complex.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N=), amino, (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl $$(-\overset{\overset{\displaystyle O}{\|}}{C}OH), \text{carbonyloxy} (-\overset{\overset{\displaystyle O}{\|}}{C}O-), \text{oxy} (-O-),$$

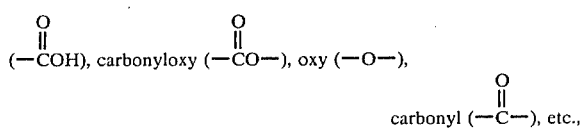

all of said groups containing Lewis base oxygen atoms. In this respect, it is the "hydroxyl" oxygen in the

and the "oxy" oxygen in the

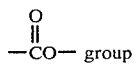

that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine, iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyrdines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methylsubstituted picolinic acid; nitrilotriacetic acid, 2,5-dicarboxypiperazine, N-(2-hydroxyethyl) iminodiacetic acid, ehtylenediamine tetraacetic acid; 2,6-dicarboxypyridine; 8-hydroxyquinoline, 2-carboxyquinoline, cyclohexane-1,2-diamine -N,N,N', N'- tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylenetetraamine, and the like. In addition any compounds capable of yielding an amino nitrogen under the reaction conditions of the present invention are promotors, as in the case of an amide, such as formamide, cyanamide, and urea, or an oxime. Further illustrative of Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di-and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',-N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like: aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine pyridine, substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino) pyridine; quinoline; substituted quinolines such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'dipyridyl, methyl-substituted 2,2-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo [2.2.2]octane, purine and the like.

Also included herein are the use of dimorpholine compounds such as ethylenedimorpholine and the other dimorpholine compounds described in U.S. patent application Ser. No. 56,967, filed July 12, 1979 (as a continuation-in-part of Ser. No. 727,645, filed Sept. 29, 1976, now abandoned) which description is incorporated herein by reference.

The promoter provided is present in an amount which is equal to or greater than that amount, determined from the promoter's basicity, which achieves the optimum rate of formation of the alkane polyol such as ethylene glycol, as described in commonly assigned copending applications Ser. Nos. 25,094 and 25,093, both filed Mar. 29, 1979 (as respective continuations of application Ser. No. 790,653, filed Apr. 25, 1977 and application Ser. No. 618,023, filed Sept. 30, 1975, both now abandoned). The disclosures of said applications Ser. Nos. 25,094 and 25,093 are incorporated herein by reference.

The concentration of the promotoer will typically be within about 0.001 to about 10 molar. Obviously this range is definitive of the potential scatter of concentrations predicated on the varieties of promoter basicity available.

Salts are also provided in the homogeneous liquid phase reaction mixture. Suitable salts include any organic or inorganic salt which does not adversely affect the production of polyhydric alcohols. Experimental work suggest that any salt is beneficial as either a copromoter and/or in aiding in maintaining rhodium in solution during the reaction. Illustrative of useful salts are the ammonium salts and the salts of the metals of Group I and Group II of the Periodic Table (Handbook of Chemistry and Physics—50th Edition) for instance the halide, hydroxide, alkoxide, phenoxide and carboxylate salts such as sodium fluoride, cesium fluoride, cesium p-methyl-sulfonylbenzoate $(CH_3SO_2C_6H_4COO)Cs$, rubidium acetate, magnesium acetate, strontium acetate, ammonium formate, ammonium benzoate and the like. Preferred are the cesium, rubidium, potassium and ammonium salts.

Also useful are organic salts of the following formula:

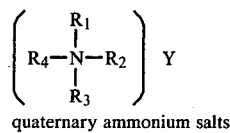

quaternary ammonium salts

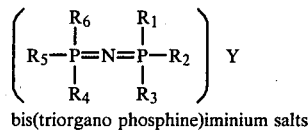

bis(triorgano phosphine)iminium salts wherein $R_1$ through $R_6$ in formulas (I) and (II) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1] heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substitued alkyl such as beta-hydroxyethyl, ethoxymethyl, ethoxyethyl, phenoxyethyl, and the like; or a polyalkylene ether group of the formula $(C_nH_{2n}O)_x$—OR wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas I and II above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas I and II, above, is a carboxylate, most preferably formate, acetate and benzoate.

A suitable method for preparing the bis(triorganophosphine) iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In addition, the anion of the above salt may be any of the rhodium carbonyl anions. Suitable rhodium carbonyl anions include $[Rh_6(CO)_{15}]^{2-}$; $[Rh_6(CO)_{15}Y]^{--}$ wherein Y may be halogen, such as chlorine, bromine, or iodine, $[Rh_6(CO)_{15}(COOR'')]_-$wherein $R''$ is lower alkyl or aryl such as methyl, ethyl, or phenyl; $[Rh_6(CO)_{14}]^{2-}$; $[Rh_7(CO)_{16}]^{3-}$; $[Rh_{12}(CO)_{30}]^{2-}$; $Rh_{13}(CO)_{24}H_3^{-2}$; and $Rh_{13}(CO)_{24}H_2^{-3}$.

The extraction solvent (as fully set forth in U.S. Pat. No. 4,001,289) may be any organic compound which has the following characteristics and relationships:

1. It is liquid under the conditions of extraction.

2. It is essentially immiscible in water, i.e., it is not more than about 10 weight percent soluble in water and water is not more than about 10 weight percent soluble in the extraction solvent. The significant aspect of this limitation is the effect compatibility of the extraction solvent with water has on the preferential extractability of the solvent for the rhodium values in the production solution. The solubility of the extraction solvent in water should not be such as to adversely affect the distribution of the rhodium values so that the undesirable amounts of rhodium are distributed in the predominantly water phase.

3. The production solvent is preferably more readily soluble in the extraction solvent than it is in water. For example, when blended with an equal volume of water and extraction solvent, determined at 25° C., and then left to stand, two liquid phases are formed, a water phase and an extraction solvent phase, and more of the production solvent is in the extraction solvent phase. This relationship is not critical, and one may characterize it by saying that the activity coefficient of the production solvent in the extraction solvent is less than the activity coefficient of the production solvent in the water phase.

4. It is essentially non-reactive with water and the alcohol products.

5. It contains a characterisitcally electron deficient atom or group which withdraws electrons from a hydrogen atom therein to cause an electron deficiency on the hydrogen atom.

In the final analysis, when the production solution is mixed with both the extraction solvent and water, each can be added to the production solution in any order, two immiscible phases must form. The water phase should carry the alcohol products and the extraction solvent phase should contain the rhodium values. The production solvent may be in either phase but will typically be in the extraction solvent phase.

The extraction solvent may be further characterized by the following test:

When the extraction solvent is intermixed at 25° C with an equal volume amount of water and the intermixture is thoroughly blended at 25° C. in a vessel of sufficient size with an equal volume of the production solution [taken from the reaction of an equal molar quantity of hydrogen and carbon monoxide fed to an autoclave at 1000 atmospheres containing 3,000 parts per million, on weight basis, of rhodium dissolved in a production solvent at 250° C. for a period of time sufficient to form a product solution containing at least 6 percent by weight of ethylene glycol], in contact with CO gas, there is formed in the vessel, on standing, two layers, one which principally contains water and the ethylene glycol and the other layer principally contains the extraction solvent and the rhodium metal content (at least 95 weight percent thereof) which was in the production solution.

In the above, water alone, will not extract the alcohol products from the production solution and the rhodium content. The extraction solvent, alone, will not separate the alcohol products from the rhodium content. It is only from a combination of the two that the alcohol products can be removed from their association with the predominant rhodium content of the production solution.

The selection of the extraction solvent as set forth in U.S. Pat. No. 4,001,289 is predicated on two interrelated, criteria, which are: (1) its relative water insolubility and (2) its preference for solubilizing the rhodium content in the production solution. Once the alcohol products are separated from the rhodium content, they are easily recovered by distillation without causing losses of rhodium.

Illustrative of specific extraction solvents which conform to the preceding criteria are, by way of example only, the following:

$CH_2Cl_2$ $CH_3Cl$ $CHCl_3$ $Cl_2CHCHCl_2$ $_2CHCH_2CHCl_2$ $Cl_3CCHClCCl_3$ $Cl_2CHCHClCHCl_2$ $CF_3CHClCF_3$ $CF_3CH_2CH_3$ $ClCH_2CH_2CH_2Si(CH_3)_3$ $ClCH_2CH_2Si(CH_3)_3$ $CH_3CH_2CN$ $CH_3CH_2CH_2CN$ $ClCH_2CH_2CN$ $NCCH_2CH_2Si(CH_3)_3$

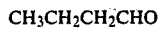
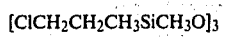
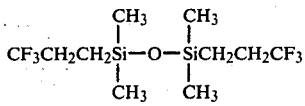
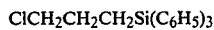
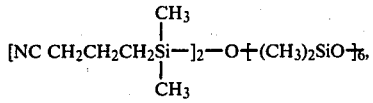
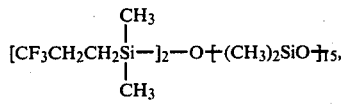
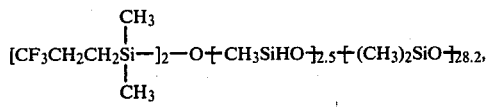
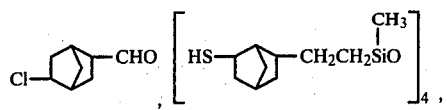
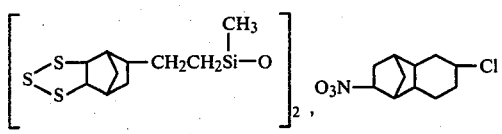

This extraction procedure involves any method which effects contact between the production solution and an amount of extraction solvent and water sufficient to remove a desired amount of alcohol product from the production solvent and retain the rhodium values in the extraction solvent phase. The ratio of water to extraction solvent may range, on a volume basis, from about 0.01 to 100, though it is preferred to use a ratio of 0.1 to 10. In the preferred embodiment, the amount of water and extraction solvent is desirably sufficient to essentially remove the alcohol products, specifically ethylene glycol, to the water phase and retain the rhodium values in a production solvent-extraction solvent phase.

Either the water or the extraction solvent may be first admixed with the production solution followed by the other. Alternatively, water and the extraction solvent may be premixed and blended with the production solution. Another procedure involves the simultaneous addition of the production solution, extraction solvent and water to a vessel with agitation.

The extraction process may be effected at ambient temperatures and pressures, though temperatures ranging from about 0° C. to about 200° C., preferably from about 15° C. to about 125° C., may be employed effectively. Pressures ranging from subatmospheric to superatmospheric pressures are suitably employed, e.g., 0.1 mm. Hg pressure to about 500 atmospheres pressures are contemplated as employable.

The improvement of the present invention is the presence of CO gas in contact with the homogeneous mixture during separation of reaction product. The carbon monoxide gas may be added to the atmosphere above a liquid body of the homogeneous mixture undergoing separation. In addition or alternatively, the CO gas can be bubbled through the liquid body.

The amount of CO gas added should be sufficient to reduce the amount of rhodium lost from the mixture when CO is not used. The carbon monoxide is provided to the mixture undergoing separation either at atmospheric pressure (i.e., 0 psig. CO) or at superatmospheric pressure such as at least about 15 pounds per square inch guage (psig.). Relative to the use of CO at atmospheric pressure, the amount of carbon monoxide provided to the mixture undergoing separation is greater when the CO pressure is superatmospheric. Thus, it is preferred to operate at a CO pressure above atmospheric. Usually, the improvement of the invention is effected at CO pressures of at least about 60, and more usually, the CO pressure is at least about 100 psig. The CO pressure may be as high as about 7500 psig. or higher, and is usually no greater than about 1000 psig.

Any of the known extraction procedures may be employed, such as mixing in a vessel with stirring followed by settling and decantation, or countercurrent extraction in which water and the extraction solvent are countercurrently fed with one premixed with the production solution, or by single direction extraction in a stirred column, and the like.

The removed alcohol products may be isolated from the water by fractional distillation and the rhodium values can be recovered by distillation of the extraction solvent or by conversion of the rhodium to an isolatable water soluble species which can thereafter be converted in a known manner for re-use in making reaction product.

The following illustrates this invention:

Table I describes data on the product solution prepared as heretofore described by reacting a mixture of hydrogen and carbon monoxide (1:1) at 8000 psig pressure, 220° C. temperature in tetraglyme solvent (75 cubic centimeters) for four hours, in the presence of a rhodium dicarbonylacetylacetonate catalyst with 1317 parts per million of pyridine. The amount of rhodium charged (parts per million), cesium salt (parts per million) as well as the weight percent of components at the end of the reaction are set forth in Table I.

TABLE I

| | | | Component Concentration (Weight percent) | | | | |
|---|---|---|---|---|---|---|---|
| Product Mixture | Rhodium (ppm) | Cesium salt (ppm cesium) | Water | Methanol | Methylformate | Ethylene Glycol | Tetraglyme |
| A | 2422 | Cesium benzoate (668) | — | 2.85 | 0.27 | 4.52 | 84.84 |
| B | 2447 | Cesium isobutyrate (718) | 0.07 | 2.82 | 0.35 | 4.51 | 92.48 |

TABLE I-continued

| | | | Component Concentration (Weight percent) | | | | |
|---|---|---|---|---|---|---|---|
| Product Mixture | Rhodium (ppm) | Cesium salt (ppm cesium) | Water | Methanol | Methylformate | Ethylene Glycol | Tetraglyme |
| C | 2440 | Cesium benzoate (776) | 0.19 | 3.00 | 0.68 | 4.26 | 90.58 |

Examples 1, 3, 5 and 9 of Table II hereinbelow are included for the purpose of comparison, no carbon monoxide having been added during the respective extractions. In Examples 1, 3 and 5, the methylene chloride extraction solvent and particular production solution were mixed in an appropriately sized separatory funnel to which water, but no carbon monoxide, was added. The contents of the funnel were shaken thoroughly by hand. Then the funnel was allowed to rest until the two liquid phases were completely separated into separate layers. Remaining Examples 2, 4 and 6-9 of Table II were conducted in a pressure vessel comprising a Jerguson gauge equipped with a mechanical stirrer sealed with a Parr packing gland. In these examples, the methylene chloride extraction solvent and particular production solution were added to the pressure vessel.

In Examples 2, 4, 6, 7 and 8, carbon monoxide was next added under the pressures given in Table II, followed by the addition of water; the contents of the pressure vessel were agitated by stirring (200 rpm). In Example 9, water was added to the methylene chloride/production solvent mixture contained in the pressure vessel but no carbon monoxide was added; agitation of the contents of the pressure vessel was effected by stirring at 200 rpm (stirring at 400 rpm caused the formation of a stable emulsion). The extractions of these various examples took from a few minutes to about 24 hours. The separate layers which formed were separated and analyzed to provide the data given in Table II which follows.

TABLE II

| Ex. | Product Mixture | Volumes (cc) Product Mixture | Volumes (cc) Water | Volumes (cc) Methylene Chloride | CO Pressure (psig) | Rhodium (ppm) Upper Layer | Rhodium (ppm) Lower Layer | Cesium (ppm) Upper Layer | Cesium (ppm) Lower Layer | Volumes (cc) Upper Layer | Volumes (cc) Lower Layer | Rh and Cs Lost to Aqueous Phase (% of Initial amt.) Rh | Rh and Cs Lost to Aqueous Phase (% of Initial amt.) Cs | Reduction of Rh Lost Due to CO (%) | Material Balance (%)[a] Rh | Material Balance (%)[a] Cs |
|---|---|---|---|---|---|---|---|---|---|---|---|---|---|---|---|---|
| 1 | A | 15 | 15 | 15 | (b) | 14.1 | 1312 | 333 | 82.5 | 20 | 25 | 0.77 | 66.0 | — | −1.17 | 11.11 |
| 2 | A | 15 | 15 | 15 | 500[c] | 0.5 | 1432 | 329 | 100.0 | 19 | 23 | 0.03 | 64.2 | 96.5 | −5.10 | 9.20 |
| 3 | B | 15 | 15 | 15 | (b) | 117.0 | 1410 | 355 | 113 | 20 | 25.5 | 6.23 | 64.4 | — | −19.94 | 4.53 |
| 4 | B | 15 | 15 | 15 | 560[c] | 9.3 | 1243 | 375 | 97.5 | 18.5 | 24.5 | 0.47 | 64.2 | 92.5 | 3.22 | 10.09 |
| 5 | C | 10 | 10 | 10 | (b) | 22.0 | 1162 | — | — | 13 | 17 | 1.18 | — | —. | 1.59 | — |
| 6 | C | 10 | 10 | 10 | 100[c] | 10.5 | 1312 | — | — | 10.5 | 17 | 0.46 | — | 65.1 | −9.51 | — |
| 7 | C | 10 | 10 | 10 | 275[c] | 5.0 | 1462 | — | — | 12 | 17 | 0.25 | — | 80.9 | −18.41 | — |
| 8 | C | 10 | 10 | 10 | 510[c] | 5.5 | 1575 | — | — | 13 | 16 | 0.30 | — | 77.0 | −20.93 | — |
| 9 | C | 10 | 10 | 10 | (d) | 26.5 | 1537 | — | — | 12 | 18 | 1.31 | — | — | −33.29 | — |

[a] A negative sign means the material balance implies a net "production" of the component.
[b] No carbon monoxide was added; hand shaken.
[c] Conducted in pressure vessel with stirring (400 rpm.).
[d] No carbon monoxide was added; conducted in pressure vessel with stirring (200 rpm.).

What is claimed is:

1. In the process of separating the alcohol products obtained by the high pressure homogeneous liquid phase reaction of oxides of carbon and hydrogen in a production solvent containing a rhodium carbonyl complex catalyst which process comprises mixing said solution with water and an organic extraction solvent in which said production solvent is more soluble than it is in water, said extraction solvent being characterized as being liquid under the conditions of the extraction as being essentially immiscible in water and as being essentially non-reactive with water and the alcohol products whereby said products are separated into an aqueous phase and the catalyst is separated into the extraction solvent phase, the improvement which comprises mixing said solution, water and extraction solvent in contact with added CO gas.

2. The process of claim 1, wherein the CO gas is at superatmospheric pressure.

3. The process of claim 2, wherein the CO pressure is at least about 100 pounds per square inch guage.

* * * * *

UNITED STATES PATENT AND TRADEMARK OFFICE
CERTIFICATE OF CORRECTION

PATENT NO. : 4,263,218
DATED : April 21, 1981
INVENTOR(S) : Steve J. Dougherty

It is certified that error appears in the above—identified patent and that said Letters Patent is hereby corrected as shown below:

Column 7, line 22, " $[Rh_6(CO)_{15}(COOR")]_-$ " should be -- $[Rh_6(CO)_{15}(COOR")]^-$ -- .

Column 8, line 47, "$_2CHCH_2CHCl_2$" should be -- $Cl_2CHCH_2CHCl_2$ -- .

Signed and Sealed this

Twentieth Day of October 1981

[SEAL]

Attest:

Attesting Officer

GERALD J. MOSSINGHOFF
Commissioner of Patents and Trademarks